United States Patent
Cousins et al.

(10) Patent No.: US 10,925,736 B2
(45) Date of Patent: *Feb. 23, 2021

(54) VALVE LEAFLET CONNECTING DEVICE

(71) Applicant: Strait Access Technologies Holdings (Pty) Ltd, Cape Town (ZA)

(72) Inventors: Michael Alan Cousins, Cape Town (ZA); Gary Steven Rowsell, Cape Town (ZA); Preyen Agasthian Perumall, Cape Town (ZA); Jeremy Douglas Jarman, Cape Town (ZA); Edward Charles Mudge, Cape Town (ZA); Travis Foster Henchie, East London (ZA); Heather Madeleine Coombes, Cape Town (ZA); Peter Paul Zilla, Cape Town (ZA); Deon Bezuidenhout, Cape Town (ZA)

(73) Assignee: Strait Access Technologies Holdings (Pty) Ltd, Cape Town (ZA)

( * ) Notice: Subject to any disclaimer, the term of this patent is extended or adjusted under 35 U.S.C. 154(b) by 0 days.

This patent is subject to a terminal disclaimer.

(21) Appl. No.: 16/622,500

(22) PCT Filed: Jun. 10, 2018

(86) PCT No.: PCT/ZA2018/050034
§ 371 (c)(1),
(2) Date: Dec. 13, 2019

(87) PCT Pub. No.: WO2018/232425
PCT Pub. Date: Dec. 20, 2018

(65) Prior Publication Data
US 2020/0375741 A1 Dec. 3, 2020

(30) Foreign Application Priority Data
Jun. 15, 2017 (GB) .................................... 1709509

(51) Int. Cl.
A61F 2/24 (2006.01)
A61B 17/068 (2006.01)
A61B 17/00 (2006.01)

(52) U.S. Cl.
CPC .......... A61F 2/2463 (2013.01); A61B 17/068 (2013.01); A61F 2/246 (2013.01);
(Continued)

(58) Field of Classification Search
CPC ...... A61F 2/2442; A61F 2/246; A61F 2/2463; A61F 2/2466; A61B 2017/00783; A61B 17/068
See application file for complete search history.

(56) References Cited

U.S. PATENT DOCUMENTS

2010/0022823 A1 1/2010 Goldfarb

FOREIGN PATENT DOCUMENTS

| WO | 0060995 A2 | 10/2000 |
| WO | 2016090308 A1 | 6/2016 |
| WO | 2016110760 A1 | 7/2016 |

OTHER PUBLICATIONS

Search Report and Written Opinion dated Oct. 4, 2019 in international Application No. PCT/ZA2018/050034.

*Primary Examiner* — William H Matthews
(74) *Attorney, Agent, or Firm* — Haugen Law Firm PLLP

(57) ABSTRACT

A valve leaflet connecting device includes: a base; and first and second followers extending from the base. A first arm extends from the first follower in a direction away from the second follower and away from the base to define an acute angle between the first follower and first arm for capturing a first leaflet there between. A second arm extends from the second follower in a direction away from the first follower and away from the base to define an acute angle between the (Continued)

second follower and second arm for capturing a second leaflet there between, The first and second followers are resiliently deformable between: (i) an open condition, in which: the point from which the first arm extends from the first follower; and the point from which the second arm extends from the second follower, are spaced more than 15 mm; and (ii) a closed condition, in which: the point from which the first arm extends from the first follower; and the point from which the second arm extends from the second follower, are spaced less than 5 mm. Deforming means deform the followers towards the closed condition. A positioner extends from the base, between the first and second followers, and a fastener releasably secured to the positioner, includes first and second fastener jaws. The first and second jaws: extend away from the base; and are movable between: (i) a splayed condition in which leaflets may be received between the first and second fastener jaws; and (ii) a securing condition in which the first and second fastener jaws secure the leaflets there between. In use: (i) the first and second followers may be: passed axially through a valve, between first and second valve leaflets; and resiliently deformed by opening and closing of the valve leaflets; (ii) the first arm may capture the first leaflet between the first arm and the first follower, and the second arm may capture the second leaflet between the second arm and the second follower, with the first and second followers disposed between the first and second leaflets; (iii) the deforming means may deform the first and second followers towards the closed condition, thereby moving the first and second leaflets towards each other; (iv) the fastener may receive the first and second leaflets between the fastener jaws when the fastener jaws are in the spayed condition; and (v) moving the fastener jaws towards the securing condition secures the first and second leaflets to each other. Alternatively, the arms and fastener jaws may extend towards the base.

21 Claims, 10 Drawing Sheets

(52) U.S. Cl.
CPC .......... *A61F 2/2442* (2013.01); *A61F 2/2466* (2013.01); *A61B 2017/00783* (2013.01); *A61F 2210/0014* (2013.01); *A61F 2230/0006* (2013.01); *A61F 2230/0008* (2013.01); *A61F 2230/0019* (2013.01)

VALVE LEAFLET CONNECTING DEVICE

BACKGROUND

The present invention relates to a valve leaflet connecting device. More particularly, the present invention relates to a device for connecting mitral valve leaflets, which device includes:
(i) a pair of resilient followers that can be disposed between valve leaflets and are sufficiently flexible and resilient (i.e. deformable) to follow the valve leaflets as they open and close;
(ii) an arm extending from each follower to capture a valve leaflet between the arm and the corresponding follower;
(iii) deforming means for moving the followers and arms towards each other; and
(iv) a positioner that locates a fastener over the free ends of the leaflets to secure the leaflets together.

Various connecting devices are known. For instance:

U.S. Pat. No. 5,015,249 "Endoscopic stapling device and method" describes a staple disposed between forceps jaws, which jaws "open" the staple (i.e. causes the staple legs to splay/diverge). Retraction of the staple within a tube "closes" the staple (i.e. causes the staple legs to move towards each other). Optionally, the forceps may also be used: to grip body tissue; and to assist in closing the staple. It will be appreciated that closure of the forceps causes the staple to close.

U.S. Pat. No. 5,403,326 "Method for performing a gastric wrap of the esophagus for use in the treatment of esophageal reflux" describes a device including an internal grasper that grasps body tissue and pulls the grasped tissue between the stapler jaws. Closure of the stapler jaws secures a staple to the grasped body tissue. It will be appreciated that closure of the stapler causes the grasper to close.

US2010/0137887 "Devices, systems and methods for tissue repair" describes a grasper that is resiliently biased towards an open condition, and outer jaws for bearing against and closing the grasper. The grasper is movable axially relative to the jaws to retract a body part grasped by the grasper for stapling. It will be appreciated that closure of the jaws causes the grasper to close.

US2010/0022823 "Methods and devices for tissue grasping and assessment" describes a fixation device that includes inner arms (with barbs) (referred to in the specification as proximal elements) that are biased towards outer jaws, and means for closing the outer jaws to capture valve leaflets between the outer jaws and inner arms. It will be appreciated that closure of the outer jaws causes the inner arms to close.

U.S. Pat. No. 3,874,388 "Shunt defect closure system" describes a pair of radially expandable, axially spaced umbrella-like elements for covering a septal defect, which umbrella-like elements may be locked in position, sandwiching the ventricular septum there between.

Similar clamping arrangements are described in U.S. Pat. No. 5,425,738 "Endoscopic anastomosis ring insertion device and method of use thereof" and US2013/0226228 "Catch member for PFO occlude" and US2014/0088640 "Delivery/recovery system for septal occlude".

A drawback of prior art connecting devices is that valve leaflets could not be captured by the connecting device while permitting continued opening and closing of the valve. In prior art connecting devices, capture of the valve leaflets/body tissue typically resulted in "closing" and clamping of the valve leaflets/body parts.

A further drawback of prior art connecting devices is that large leaflet capture means are required to capture valve leaflets while the valve opens and closes. Furthermore, a complex control is required to position the leaflet capture means in the correct position to effect satisfactory capture of valve leaflets. In prior art connecting devices, the large capture means resulted in large connecting devices and delivery and access systems.

It is an object of the present invention to provide a valve leaflet connecting device that: includes a follower for following valve leaflets as they open and close; captures valve leaflets while continuing to permit the valve leaflets to open and close; and only after properly capturing the valve leaflets in such manner, causes the valve leaflets to move to a closed condition to facilitate connecting of the valve leaflets to each other.

SUMMARY OF THE INVENTION

According to a preferred embodiment of the invention, there is provided a valve leaflet connecting device that includes:
 a base that defines a longitudinal axis;
 first and second followers extending from the base;
 a first arm on the first follower, which first arm extends from the first follower in a direction away from the second follower and away from the base to define an acute angle between the first follower and first arm for capturing a first leaflet there between;
 a second arm on the second follower, which second arm extends from the second follower in a direction away from the first follower and away from the base to define an acute angle between the second follower and second arm for capturing a second leaflet there between;
 the first and second followers being resiliently deformable between:
  an open condition, in which:
   a first virtual line that: intersects the point from which the first arm extends from the first follower; and runs parallel to the longitudinal axis of the base; and
   a second virtual line that: intersects the point from which the second arm extends from the second follower; and runs parallel to the longitudinal axis of the base,
  are spaced more than 15 mm; and
  a closed condition, in which the first and second virtual lines are spaced less than 5 mm; and
 deforming means for deforming the followers towards the closed condition;
 such that, in use:
(i) the first and second followers may be: passed axially through a valve, between first and second valve leaflets; and resiliently deformed by opening and closing of the valve leaflets;
(ii) the first arm may capture the first leaflet between the first arm and the first follower, and the second arm may capture the second leaflet between the second arm and the second follower, with the first and second followers disposed between the first and second leaflets; and
(iii) the deforming means may deform the first and second followers towards the closed condition, thereby moving the first and second leaflets towards each other.

Typically, the valve leaflet connecting device according to the preferred embodiment of the invention further includes:
 a positioner extending from the base, between the first and second followers; and
 a fastener releasably secured to the positioner, which fastener includes first and second fastener jaws that:

extend away from the base; and
are movable between: (i) a splayed condition in which leaflets may be received between the first and second fastener jaws; and (ii) a securing condition in which the first and second fastener jaws secure the leaflets there between, such that, in use, when first and second leaflets are moved towards each other:

(i) the fastener may receive the first and second leaflets between the fastener jaws when the fastener jaws are in the spayed condition; and
(ii) moving the fastener jaws towards the securing condition secures the first and second leaflets to each other.

According to an alternative embodiment the invention, there is provided a valve leaflet connecting device that includes:

a base that defines a longitudinal axis;
first and second followers extending from the base;
a first arm on the first follower, which first arm extends from the first follower in a direction away from the second follower and towards the base to define an acute angle between the first follower and first arm for capturing a first leaflet there between;
a second arm on the second follower, which second arm extends from the second follower in a direction away from the first follower and towards the base to define an acute angle between the second follower and second arm for capturing a second leaflet there between;
the first and second followers being resiliently deformable between:
an open condition, in which:
a first virtual line that: intersects the point from which the first arm extends from the first follower; and runs parallel to the longitudinal axis of the base; and
a second virtual line that: intersects the point from which the second arm extends from the second follower; and runs parallel to the longitudinal axis of the base,
are spaced more than 15 mm; and
a closed condition, in which the first and second virtual lines are spaced less than 5 mm; and
deforming means for deforming the followers towards the closed condition,
such that, in use:
(i) the first and second followers may be: passed axially through a valve, between first and second valve leaflets; and resiliently deformed by opening and closing of the valve leaflets;
(ii) the first arm may capture the first leaflet between the first arm and the first follower, and the second arm may capture the second leaflet between the second arm and the second follower, with the first and second followers disposed between the first and second leaflets; and
(iii) the deforming means may deform the first and second followers towards the closed condition, thereby moving the first and second leaflets towards each other.

Typically, the valve leaflet connecting device according to the alternative embodiment of the invention further includes:
a positioner extending from the base, between the first and second followers; and
a fastener releasably secured to the positioner, which fastener includes first and second fastener jaws that: extend towards the base; and
are movable between: (i) a splayed condition in which leaflets may be received between the first and second fastener jaws; and (ii) a securing condition in which the first and second fastener jaws secure the leaflets there between, such that, in use, when first and second leaflets are moved towards each other:
(i) the fastener may receive the first and second leaflets between the fastener jaws when the fastener jaws are in the spayed condition; and
(ii) moving the fastener jaws towards the securing condition secures the first and second leaflets to each other.

According to Both the First and Second Embodiments of the Invention

Typically: (i) the first arm extends from the first follower by at least 3 mm; and (ii) the second arm extends from the second follower by at least 3 mm.

Generally, the valve leaflet connecting device further includes a catheter, and wherein the base is disposed at, or defined by a first axial end of the catheter.

Preferably, the first and second followers and the positioner: (i) extends from an axially extending lumen defined by the catheter and the base; and (ii) are movable axially along the axially extending lumen defined by the catheter.

Typically, the valve leaflet connecting device further includes control means at or near a second axial end of the catheter for:
controlling relative axial movement of the catheter on the one hand and the first and second followers on the other hand;
controlling relative axial movement of the catheter and the positioner, thereby to vary the position of the fastener relative to the first and second arms; and
controlling movement of the fastener jaws from the splayed condition to the securing condition.

Optionally, the first arm is hingedly connected to the first follower and the second arm is hingedly connected to the second follower.

Further optionally, the first and second arms are movable along the first and second followers, respectively. Furthermore, the first arm may be movable along the first follower independently of movement of the second arm along the second follower.

Even further optionally, the valve leaflet connecting device further includes clamping means for moving the first and second arms from: (i) a receiving condition, in which free ends of the first and second arms are spaced from the first and second followers, respectively, for receiving leaflets there between; and (ii) a clamped condition, in which the first and second arms are biased towards the first and second followers, respectively, for clamping leaflets there between.

The clamping means may be operable independently or the deforming means.

Generally, each of the first and second followers define: (i) a diverging zone proximal the base, along which diverging zone the first and second followers diverge from each other as they extend from the base; and (ii) a converging zone, along which the first and second followers converge towards each other as they extend from the end of the diverging zone distal the base.

Preferably: (i) the diverging zones on the first and second followers extend from the base to the first and second arms, respectively; and (ii) the converging zones on the first and second followers extend from the first and second arms, respectively to free ends of the first and second followers.

Typically, in respect of the second embodiment of the invention the invention:

each of the first and second followers comprises: (i) a first portion that extends from the base and terminates prior to the points at which the first and second arms extend from the first and second followers, respectively; and (ii) a second portion that extends from the terminus of the first portion to free ends of the first and second followers, respectively; and in respect of each of the first and second follower, the first portion is releasably secured to the second portion.

Optionally, the fastener is aligned with the first and second arms, such that: (i) the first and second arms may be received between the fastener jaws when the fastener jaws are in the splayed condition; and (ii) subsequent movement of the fastener jaws towards the securing condition causes the first and second arms to clamp against the first and second followers, respectively.

The valve leaflet connecting device may further include hingedly connected stabilising jaws disposed between the first and second followers, the ends of the stabilising jaws distal the hinge being connected to the first and second followers and the hinged connection of the stabilising jaws being:

located between the first and second followers; and
spaced from the base,
such that deformation of the first and second followers between the open and closed conditions causes the hinged connection of the stabilising jaws to displace relative to the base.

Furthermore, the valve leaflet connecting device may further include resisting means for resisting displacement of the hinged connection of the stabilising jaws relative to the base, thereby to vary stiffness of the first and second followers.

Optionally, according to a valve leaflet connecting device according to the alternatively embodiment of the invention, the first and second arms may be resilient and may be axially retractable within, and extendable from the first and second followers, respectively.

Alternatively, according to a valve leaflet connecting device according to the preferred embodiment of the invention, each of the first and second followers may be bifurcated towards its free end, for receiving the fastener between the bifurcations.

BRIEF DESCRIPTION OF THE DRAWINGS

The invention will now be described in more detail, by way of examples only, with reference to the accompanying drawings in which.

DESCRIPTION OF THE INVENTION

Figure 1:
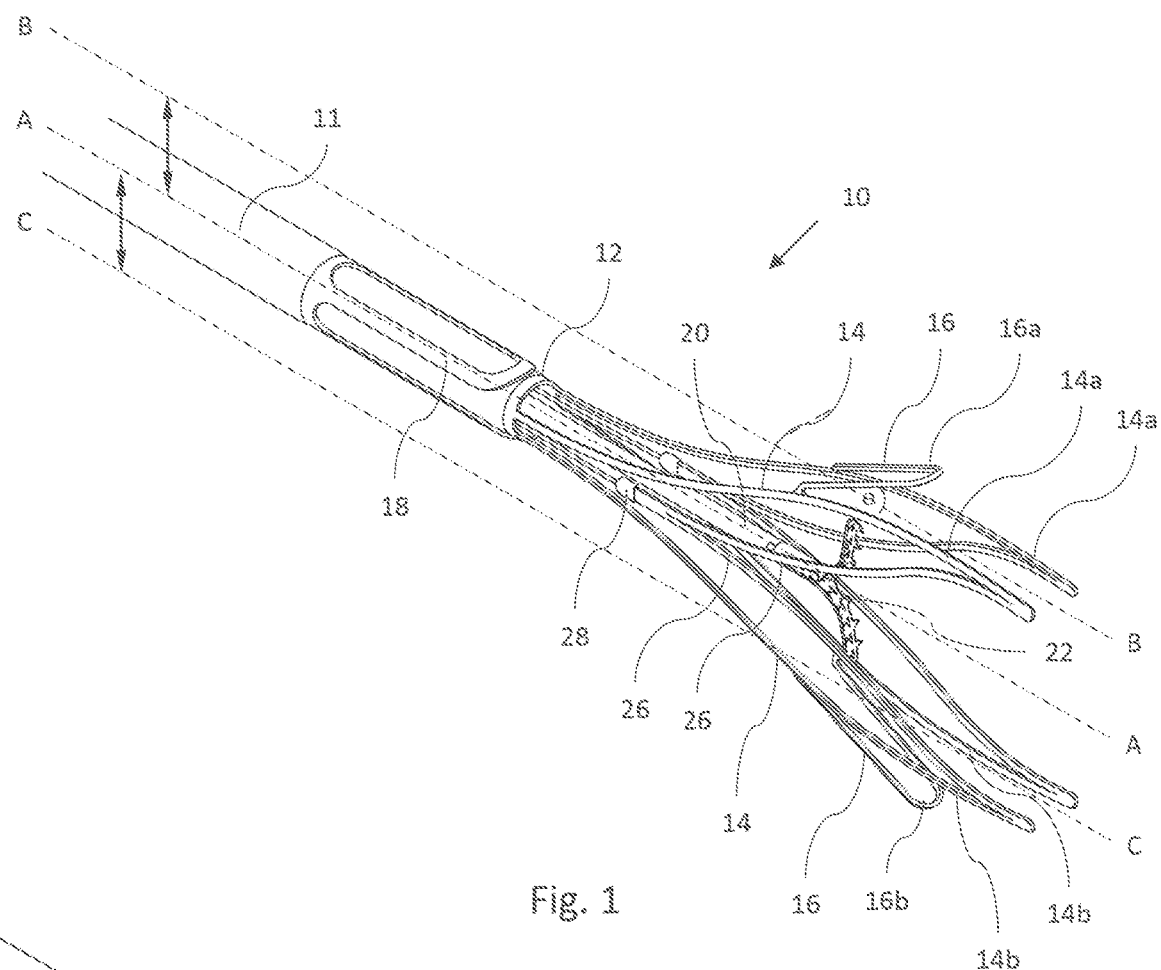
FIG. 1 is a perspective view of a valve leaflet connecting device according to a preferred embodiment of the invention, with followers in an open condition.

With reference to FIGS. 1 to 6 of the drawings, a valve leaflet connecting device 10 according to a preferred embodiment of the invention includes a catheter 11, base 12, first and second followers 14, first and second arms 16, deforming means 18, a positioner 20 and a fastener 22.

Figure 2:
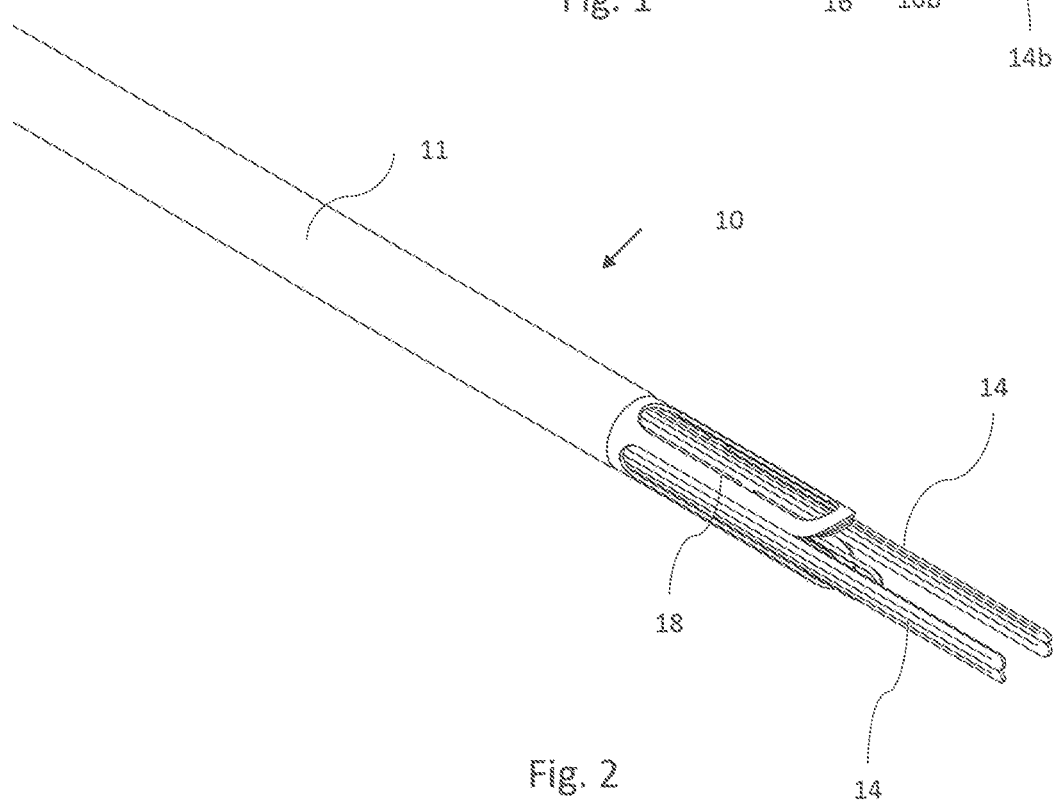
FIG. 2 is a perspective view of the valve leaflet connecting device in FIG. 1, in a crimped condition.

The valve leaflet connecting device 10 can be configured into a crimped condition shown in FIG. 2 for insertion of the valve leaflet connecting device 10 into and through a patient's vasculature or anatomy. When the base 12 is adjacent a patient's valve, more specifically a heart valve, even more specifically a mitral valve or tricuspid valve, the valve leaflet connecting device 10 can be configured to the condition shown in FIG. 1 to: pull the mitral valve leaflets 24 towards each other (i.e. towards a closed condition); and connect/clip the free ends of the mitral valve leaflets 24 together.

The catheter 11 comprises a flexible tube sized and shaped to facilitate passage through a patient's vasculature or anatomy. The catheter defines a longitudinal axis. Controls (not shown) are disposed at a first axial end of the catheter 11, whereas the base 12, followers 14 (with arms 16), positioner 20 and fastener 22 extend from a second axial end of the catheter 11.

The base 12 is secured to the second axial end of the catheter 11. Alternatively, the base 12 could be made integrally with the second axial end of the catheter 11. The base 12 defines a common longitudinal axis (shown as A-A on FIG. 1) with the catheter 11.

Each follower 14 comprises a resilient, elongate member. FIG. 1 shows each follower 14 as a bifurcated member, bifurcating/diverging from the base 12 towards the free end of the follower 14. The followers 14 may be movable axially relative to the base 12 and catheter 11. The followers 14 are biased to diverge from each other towards the free ends of the followers 14. When not deformed by external forces, each follower 14 is substantially S-shaped. In other words, each follower 14 is curved and defines a single inflection point, substantially mid-way along its length. More particularly, each of the first and second followers 14a and 14b defines:

(i) a diverging zone proximal the base 12, along which diverging zone the first and second followers 14a and 14b diverge from each other as they extend from the base 12; and (ii) a converging zone, along which the first and second followers 14a and 14b converge towards each other as they extend from the end of the diverging zone distal the base 12.

Preferably, the followers 14 are made of nitinol. Deformation of the followers 14 could be regulated by variation in cross-sectional geometry (e.g. circular, oval, rectangular) along the length of each follower 14. In addition, living hinges could be incorporated into the followers 14 to facilitate hinged deformation at desired points along the followers 14.

An arm 16 extends from each follower 14. Preferably, each arm 16 is connected to, and extends from a point on its corresponding follower 14 closer to the free end of the follower than to the base 12 (i.e. within a region from the free end of the follower 14 to a point halfway towards the base 12). More preferably, each arm 16 is connected to the corresponding follower 14 within the region from the free end of the follower 14 to a point a third of the length along the follower 14 (i.e. the end one-third of the follower 14).

Preferably, the arms 16 are located at the point of inflection along the followers 14 (i.e. at the junction of the diverging and converging zones of the followers 14).

Typically: (i) the diverging zones on the first and second followers 14a and 14b extend from the base 12 to the first and second arms 16a and 16b, respectively; and (ii) the converging zones on the first and second followers 14a and 14b extend from the first and second arms 16a and 16b, respectively to the free ends of the first and second followers 14a and 14b.

Figure 7:
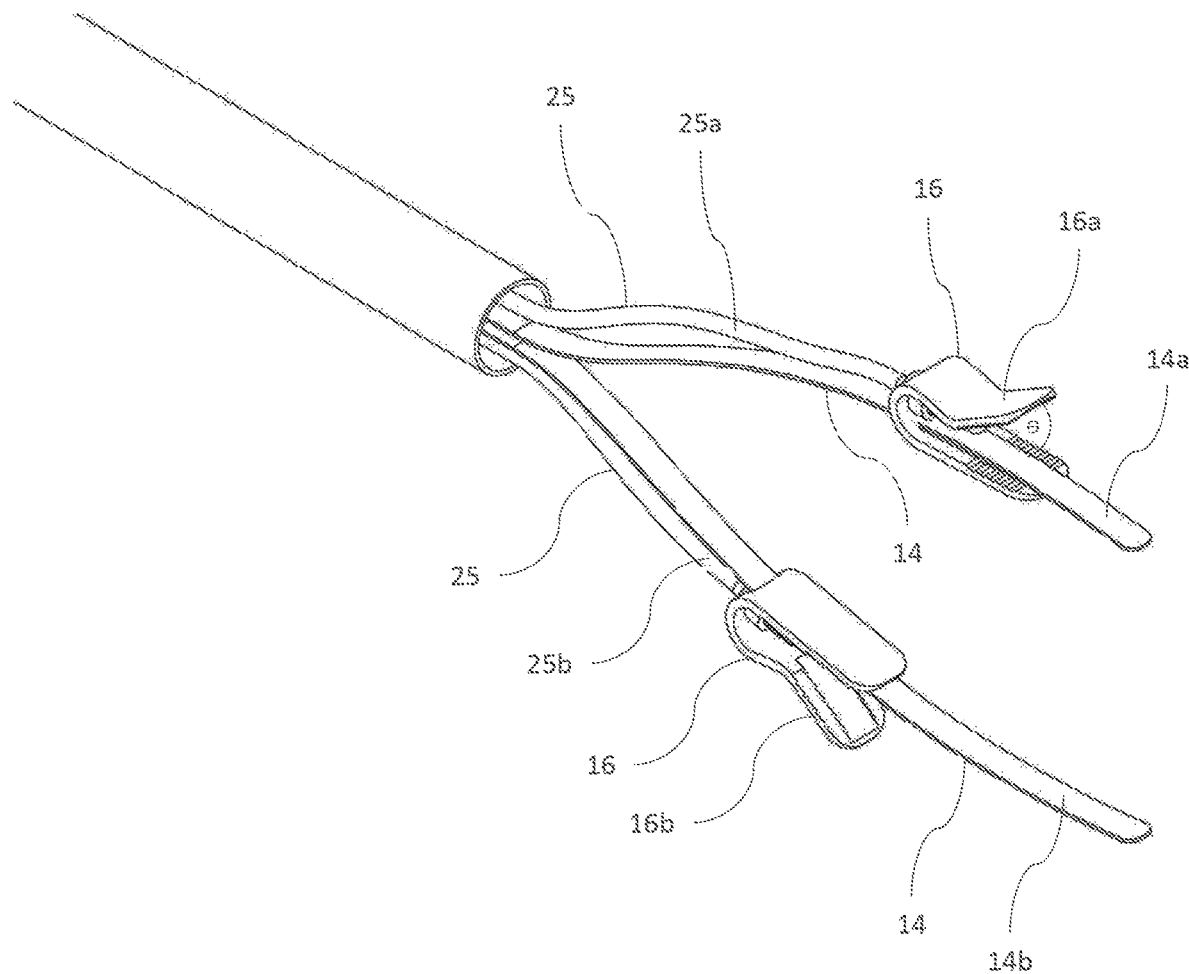
FIG. 7 is a perspective view of an alternative arrangement of an arm on a follower.

Optionally, as shown in FIG. 7, each arm 16 could be hingedly connected to its corresponding follower 14 to enable the arm 16 to pivot towards its corresponding follower 14, reducing the angle (Θ) there between. Further optionally, but not shown, each arm 16 could be movable along its corresponding follower 14 using its corresponding arm actuator 25, i.e. towards the free end of the follower 14. Specifically, arms 16a and 16b could be movable along their corresponding followers 14a and 14b using their corresponding arm actuators 25a and 25b independently of one another, i.e. arms 16a and 16b could be movable on their corresponding followers 14a and 14b to different positions along their respective followers 16a and 16b. This could allow for capturing and repositioning of leaflets 24 that are not aligned with one another, e.g. a prolapsed valve leaflet. Even further optionally, the valve leaflet connecting device 10 could further include clamping means (not shown) for moving the first and second arms 16a and 16b from: (i) a receiving condition, in which free ends of the first and second arms 16a and 16b are spaced from the first and second followers 14a and 14b, respectively, for receiving valve leaflets 24 there between; and (ii) a clamped condition, in which the first and second arms 16a and 16b are biased towards the first and second followers 14a and 14b, respectively, for clamping valve leaflets 24 there between. The clamping means and movement of the arms 16 along the followers 14 could be controlled by the controller. It will be appreciated that, if the first and second arms 16a and 16b are hingedly connected to the first and second followers 14a and 14b, respectively, movement of the arms 16 to the clamping condition by the clamping means does not cause the followers 14 to move towards each other.

Returning to the preferred embodiment, FIGS. 1 to 6 show:
(i) the first arm 16a extending from the first follower 14a by at least 3 mm in a direction away from the second follower 14b and away from the base 12 to define an acute angle (Θ) between the first follower 14a and first arm 16a; and
(ii) the second arm 16b extending from the second follower 14b by at least 3 mm in a direction away from the first follower 14a and away from the base 12 to define an acute angle (Θ) between the second follower 14b and second arm 16b.

The first and second followers 14a and 14b are resiliently deformable between:
(i) an open condition shown in FIG. 1, in which:
 a first virtual line B-B that: intersects the point from which the first arm 16a extends from the first follower 14a; and runs parallel to the longitudinal axis A-A of the base 12; and
 a second virtual line C-C that: intersects the point from which the second arm 16b extends from the second follower 14b; and runs parallel to the longitudinal axis A-A of the base 12,
 are spaced more than 15 mm; and
(ii) a closed condition, shown in FIG. 4, in which the first and second virtual lines B-B and C-C (shown in FIG. 1) are spaced less than 5 mm.

It will be appreciated that the term "spaced" in relation to the first and second virtual lines B-B and C-C refers to spacing along a line that extends orthogonally between the first and second virtual lines A-A and B-B.

The deforming means 18 comprises a tubular collar or sheath located over the second axial end of the catheter 11/the base 12. The deforming means 18 is axially movable relative to the catheter 11/the base 12 between: (i) a retracted condition, in which the deforming means is wholly located over the base 12 and/or the catheter 11; and (ii) an extended condition, in which the deforming means 18 protrudes at least 15 mm axially beyond the axial end of the base 12 distal the catheter 11. Optionally, the deforming means 18 could be moved along the followers 14 to abut the arms 16. As the deforming means 18 moves from the retracted condition to the extended condition, the deforming means 18 bears against and deforms the followers 14 from the open condition to the closed condition. When the followers 14 are in the closed condition, the followers 14 are preferably aligned substantially parallel relative to each other.

Where the valve leaflet connecting device 10 includes a clamping means, the clamping means is operable independently or the deforming means 18.

The positioner 20 is a flexible rod that extends from the centre of the base 12 and that is movable relative to the base 12 along a path that represents an extension of the longitudinal axis of the base 12/catheter 11. The positioner 20 is movable between: (i) a stowed condition, in which the positioner 20 does not protrude more than 5 mm axially beyond the axial end of the base 12 distal the catheter 11; and (ii) a locating condition, in which the positioner 20 protrudes at least 15 mm axially from the axial end of the base 12 distal the catheter 11.

The first follower 14a with first arm 16a on the one hand and the second follower 14b with second arm 16b on the other hand are substantially mirrored along a path that represents an extension of the longitudinal axis of the base 12/catheter 11. Accordingly, the positioner 20 moves along the centre-line between the first follower 14a and the second follower 14b.

The fastener 22 is disposed on, and releasable secured to the free axial end of the positioner 20. The fastener 22 is shown in the form of a clip with pivotally connected first and second fastener 22 jaws that extend from their pivotal connection away from the base 12. The fastener 22 jaws are movable between: (i) a splayed condition in which valve leaflets 24 may be received between the first and second fastener 22 jaws; and (ii) a securing condition in which the first and second fastener 22 jaws secure the valve leaflets 24 there between. The fastener 22 may be moved to the securing condition by pushing a fastener sheath over the fastener 22 jaws.

When the valve leaflet connecting device 10 is in the crimped condition, the followers 14 (with arms 16) and the positioner 20 (with fastener 22) may be fully retracted within the base 12/lumen defined by the catheter 11, to facilitate movement of the valve leaflet connecting device 10 through a patient's vasculature or anatomy.

The controls regulate:
(i) movement of the followers 14 (with arms 16) and the positioner 20 (with fastener 22) axially relative to the base 12;
(ii) movement of the deforming means 18 between the retracted condition and the extended condition;
(iii) movement of the arms 16 relative to the followers 14;
(iv) movement of the followers 14 from the open condition to the closed condition;
(v) movement of the positioner 20 between the stowed condition and the locating condition;
(vi) movement of the fastener 22 between the splayed condition and the securing condition; and
(vii) disconnection of the fastener 22 from the positioner 20.

The valve leaflet connecting device 10 further includes hingedly connected stabilising jaws 26 disposed between the first and second followers 14a and 14b. The ends of the stabilising jaws 26 distal the hinge connecting the stabilising jaws 26 are connected to the first and second followers 14a and 14b, and the hinged connection of the stabilising jaws 26 are:
  located between the first and second followers 14a and 14b; and
  spaced from the base 12,
  such that deformation of the first and second followers 14a and 14b between the open and closed conditions causes the hinged connection of the stabilising jaws 24 to displace relative to the base 12.

Optionally, with specific reference to FIG. 1, resisting means 28 may vary resistance to displacement of the hinged connection of the stabilising jaws 26 relative to the base 12, thereby to vary stiffness of the first and second followers 14a and 14b. Varying the stiffness of the followers 14 is useful to ensure that the followers 14 remain engaged with the valve leaflets 24 during opening and closing of the valve leaflets 24.

Figure 3:
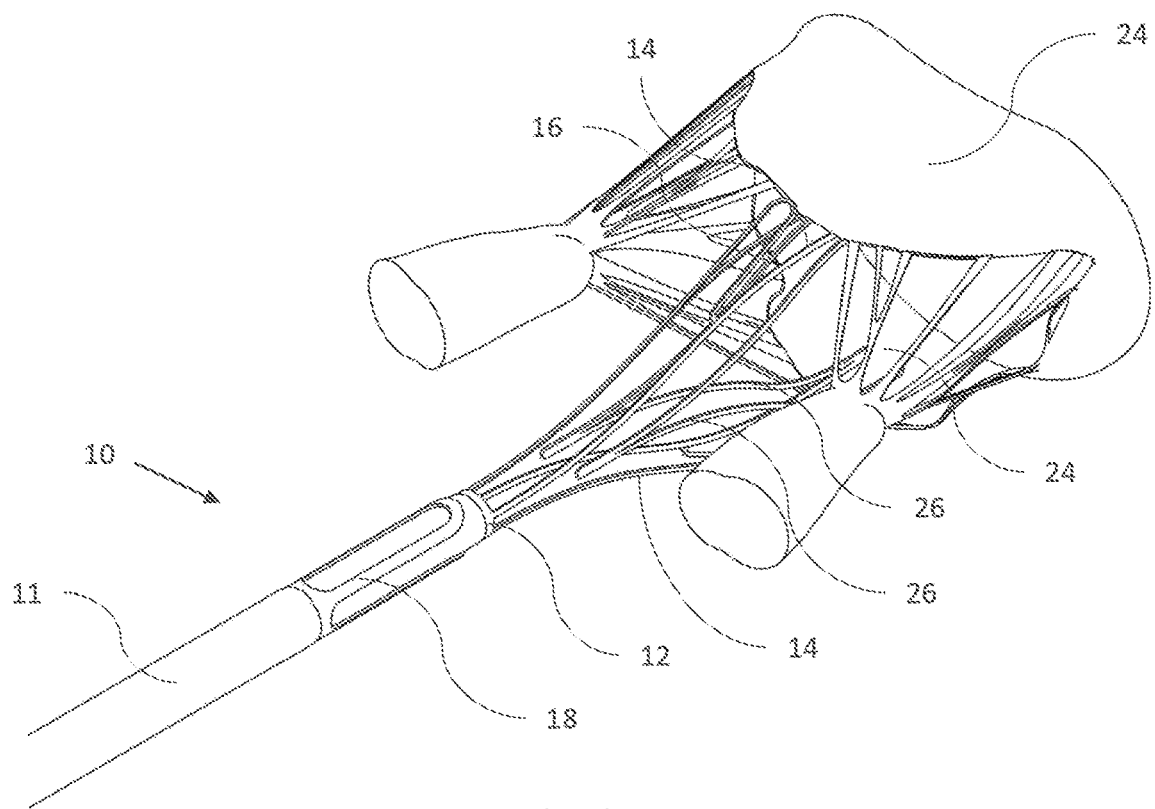
FIG. 3 is a perspective view of the valve leaflet connecting device in FIG. 1, with the followers extending through mitral valve leaflets and the followers in the open condition.
Figure 4:
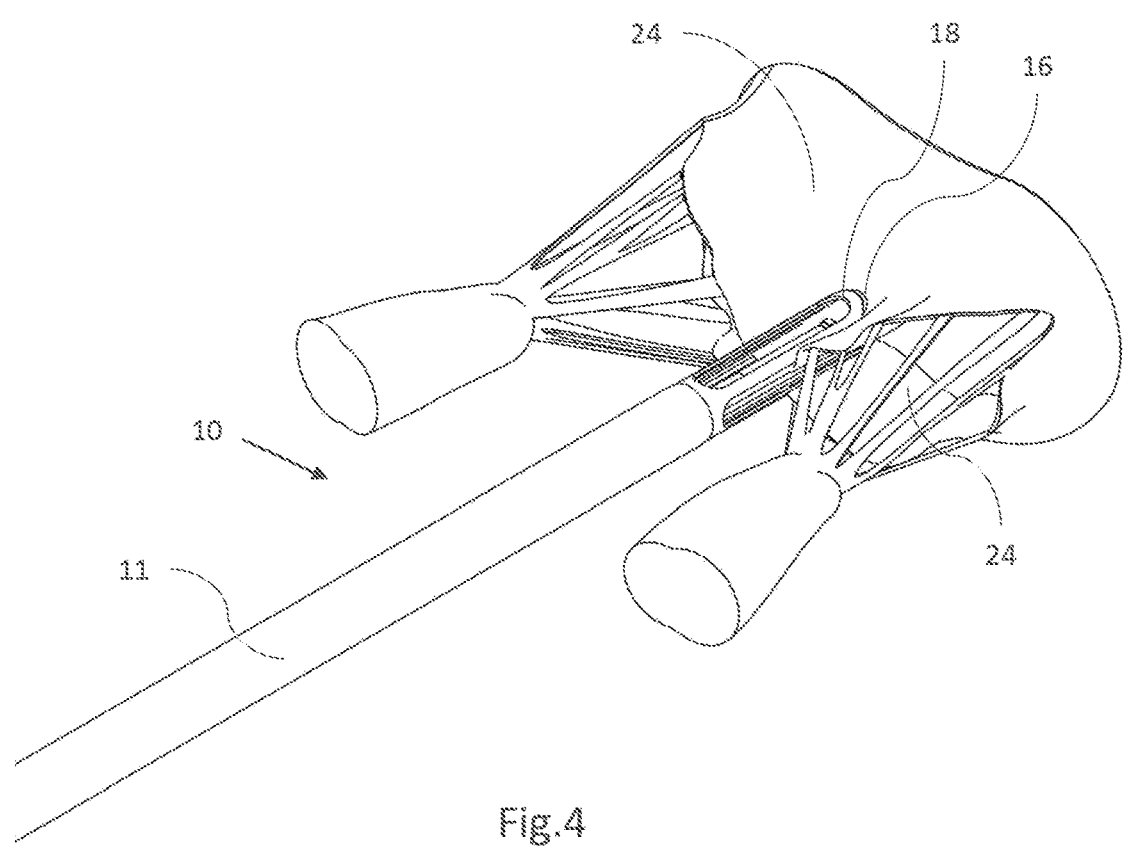
FIG. 4 is a perspective view of the valve leaflet connecting device in FIG. 3, with the followers in a closed condition.
Figure 5:
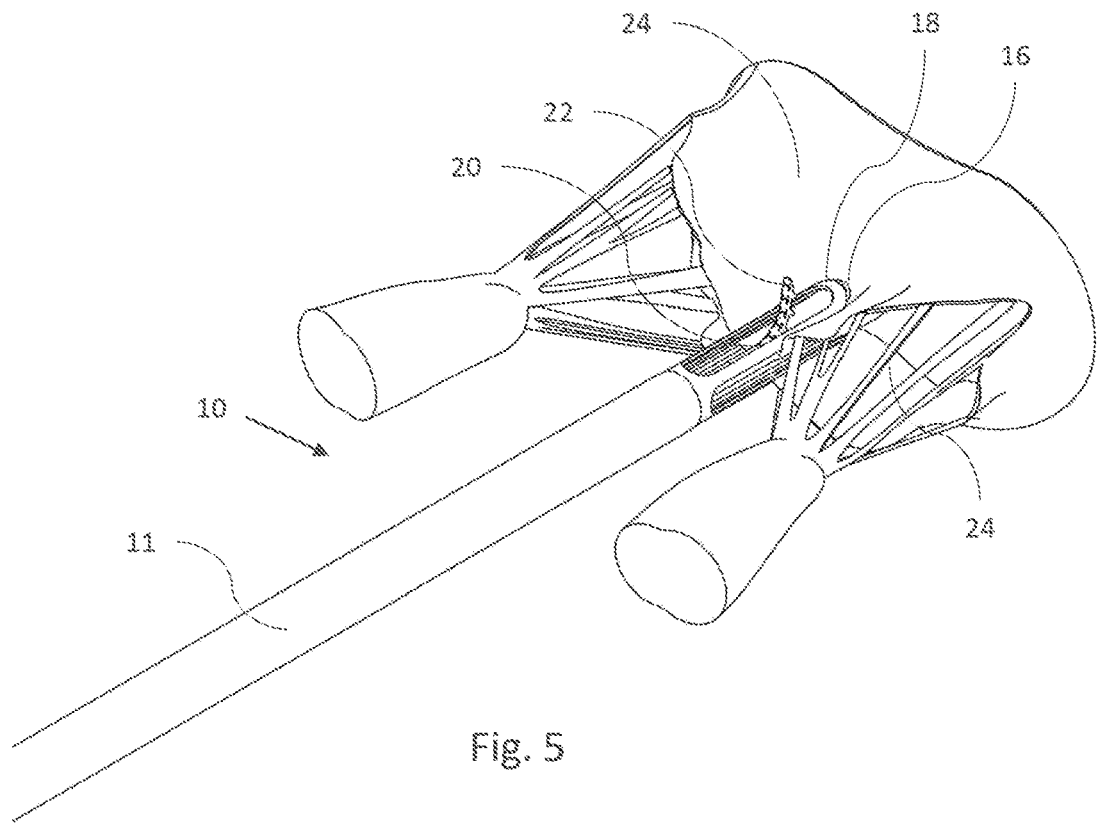
FIG. 5 is a perspective view of the valve leaflet connecting device in FIG. 3, with a positioner locating a fastener over mitral valve leaflets.
Figure 6:
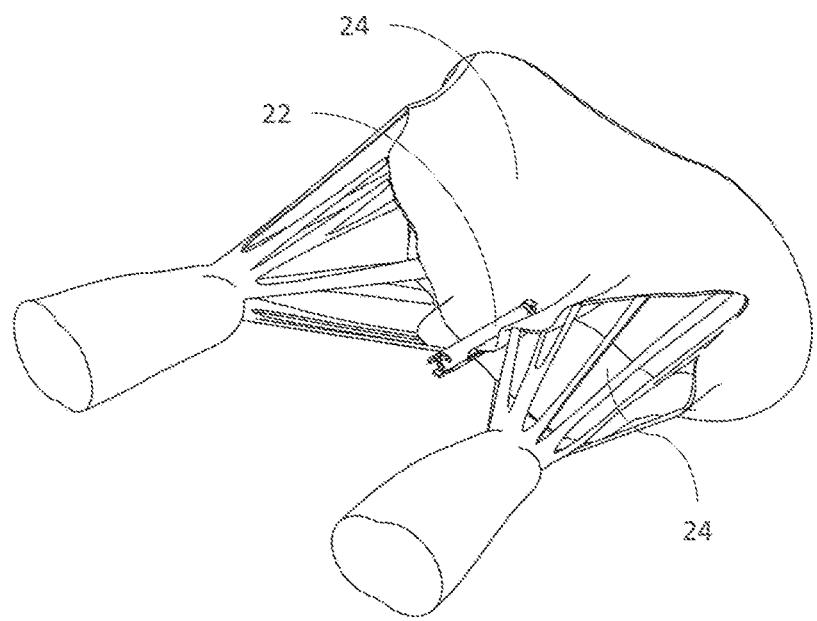
FIG. 6 is a perspective view of the valve leaflet connecting device in FIG. 3, after detachment of the fastener.
Figure 8:
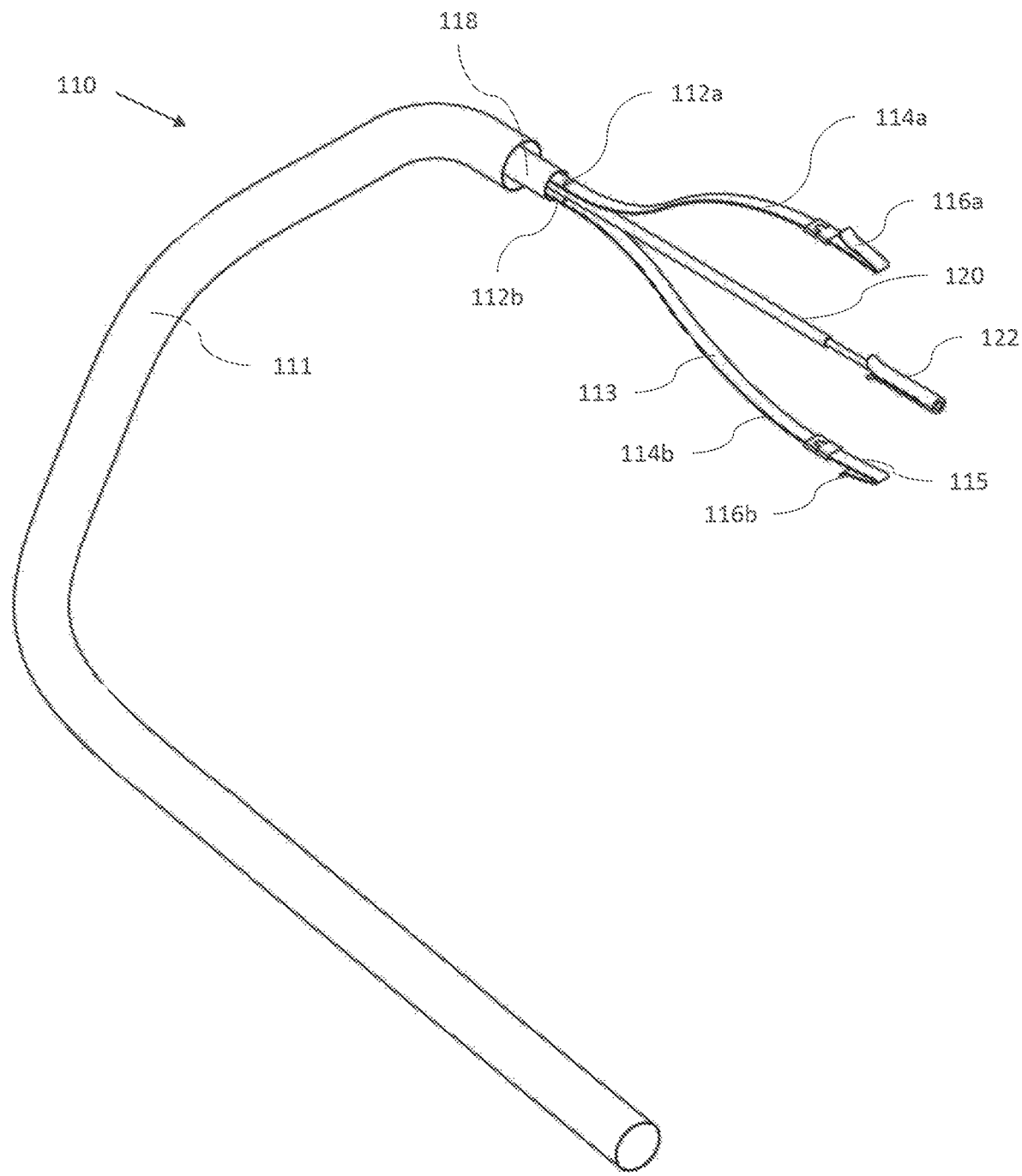
FIG. 8 is a perspective view of a valve leaflet connecting device according to an alternative embodiment of the invention, with followers in an open condition.

In use:
  With the valve leaflet connecting device 10 configured in the crimped condition shown in FIG. 2, the valve leaflet connecting device 10 (excluding the controls which remain outside the body) is threaded via a patient's vasculature or anatomy to a mitral valve.
  The free ends of the first and second followers 14a and 14b are passed axially through the mitral valve, between first and second valve leaflets 24.
  The deforming means 18 is moved from the extended to the retracted condition to enable the followers 14 to splay (under their own resilient bias) towards the open condition, as shown in FIG. 3.
  The flexibility and resilience of the followers 14 (as may be varied by the resisting means) permits the followers to move in sympathy with opening and closing of the valve leaflets 24, thereby maintaining contact between the followers 14 and valve leaflets 24 throughout the cardiac cycle.
  The followers 14 and/or arms 16 are then moved into position relative to the valve leaflets 24 such that: a first valve leaflet 24 is captured between the first follower 14a and first arm 16a (within the acute angle ($\Theta$) defined there between), and a second valve leaflet 24 is captured between the second follower 14b and second arm 16b (within the acute angle ($\Theta$) defined there between). The capture of valve leaflet 24 between followers 14 and arms 16 may be achieved without active control of follower 14 and/or arm 16 as follower 14 opens and closes in sympathy with valve leaflet 24, maintaining contact with valve leaflet 24 throughout the cardiac cycle and allowing passive positioning of arm 16 at the free edge of valve leaflet 24. Additionally, the passive positioning of arm 16 may allow for miniaturisation of arm 16 as follower 14 positions arm 16 at the free edge of valve leaflet 24 when valve leaflet 24 is in an open condition or closed condition or in any condition there between. That is, arm 16 need not be of a size to capture valve leaflets 24 as the valve opens and closes. Optionally, this step may include the following additional steps:
    (i) moving the arms 16 along the followers 14 (towards the free ends of the followers 14) to receive the valve leaflets 24 between the arms 16 and corresponding followers 14; and
    (ii) actuating clamping means to cause the arms 16 to pivot relative to the corresponding followers 14 to reduce the acute angle ($\Theta$) there between and to clamp the leaflets 24 between the followers 14 and arms 16.
  Optionally, (and shown incidentally in FIGS. 8 and 9), each follower 14 may be movable axially relative to each other to enable a follower 14 to: capture a prolapsed valve leaflet 24; and to bring the prolapsed valve leaflet 24 in apposition with its opposing leaflet 24. Alternatively optionally, as shown in FIG. 7, the arms 16 may independently movable along their followers 14 to capture a prolapsed valve leaflet 24; and to bring the prolapsed valve leaflet 24 in apposition with its opposing leaflet 24.
  With the valve leaflets 24 effectively secured between the arms 16 and followers 14, the deforming means 18 is moved from the retracted condition towards the extended condition to cause the followers 14 to deform from the open condition to the closed condition, as shown in FIG. 4, thereby pulling the valve leaflets 24 towards each other.
  With the valve leaflets 24 held in the closed position by the arms 16 and followers 14, the positioner 20 moves from the stowed condition to the locating condition, between the bifurcated followers 14, as shown in FIG. 5, thereby moving the fastener 22 (with its jaws in the spayed condition) towards the free edges of the valve leaflets 24, between the bifurcated followers 14.
  With the valve leaflets 24 extending between the splayed fastener 22 jaws of the fastener 22, the fastener 22 jaws are moved from the splayed condition to the securing condition, thereby clamping/stapling the valve leaflets together in the vicinity of the valve leaflet 24 free ends.
  The fastener 22 is then disconnected from the positioner 20, as shown in FIG. 6, and the valve leaflet connecting device 10 configured back to the crimped condition to facilitate removal of the valve leaflet connecting device 10 (excluding the fastener 22) from the patient's vasculature or anatomy.

Figure 9:
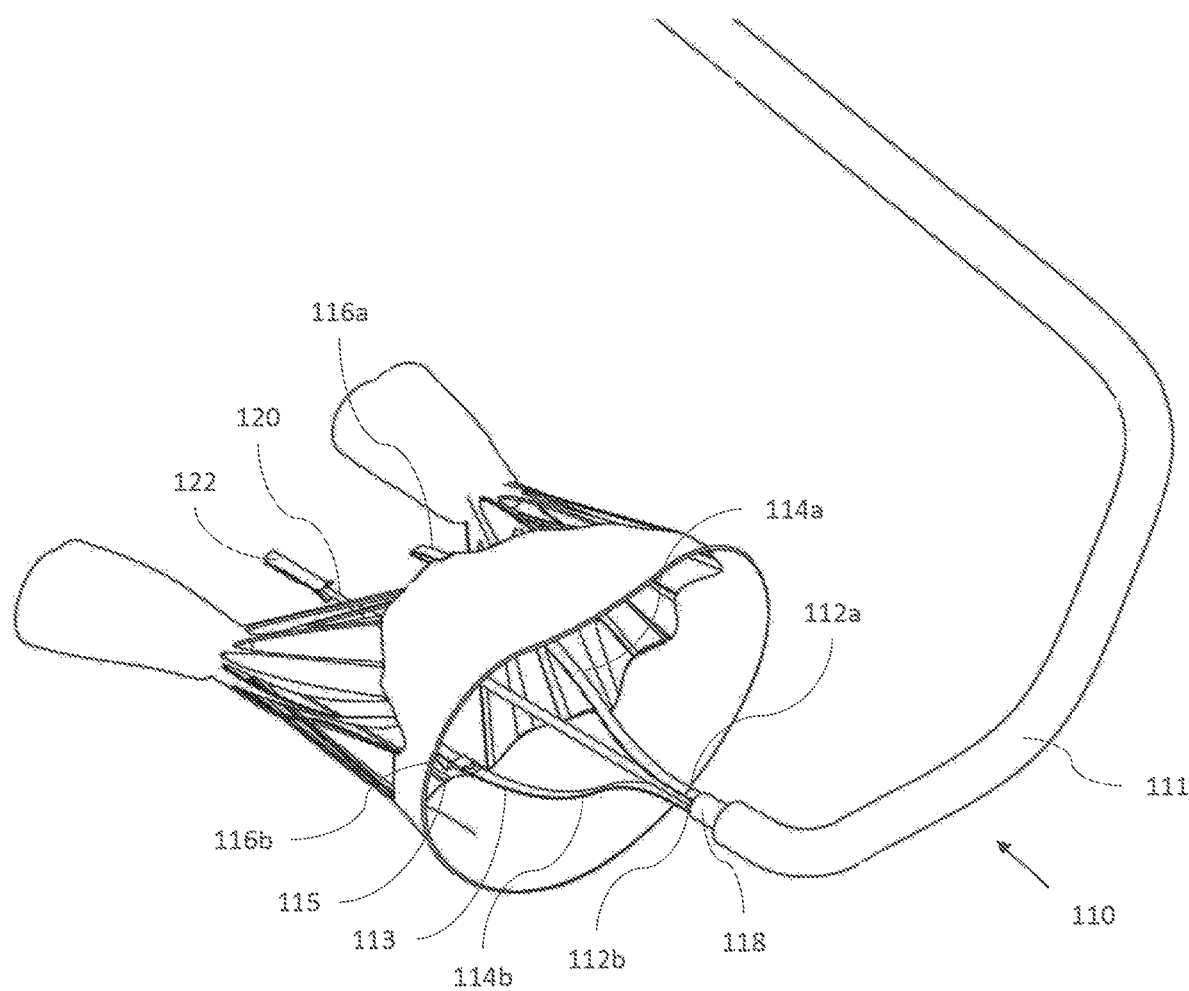
FIG. 9 is a perspective view of the valve leaflet connecting device in FIG. 8, with the followers extending through mitral valve leaflets and the followers in the open condition.

A second embodiment of the valve leaflet connecting device 110 is shown in FIGS. 8 to 12. Generally, the second embodiment of the valve leaflet connecting device 110 is similar to the preferred embodiment of the valve leaflet connecting device 10, in that the valve leaflet connecting device 110 includes a similar catheter 111, base 112, controller, positioner 120 and deforming means 118. However:

the direction of the arms 116 and the fastener 122 is reversed, in that the arms 116 and fastener 122 are directed towards the base 112. Put another way, in this arrangement:

the first arm 116a extends from the first follower 114a in a direction away from the second follower 114b and towards the base 112 to define an acute angle between the first follower 114a and first arm 116a for capturing a first valve leaflet 24 there between (as shown in FIG. 9);

the second arm 116b extends from the second follower 114b in a direction away from the first follower 114a and towards the base 112 to define an acute angle between the second follower 114b and second arm 116b for capturing a second valve leaflet 24 there between (as shown in FIG. 9); and the fastener 122 first and second jaws extend towards the base 112; and each of the first and second followers 114a and 114b comprises: (i) a first portion 113 that extends from the base 112 and terminates prior to the points at which the first and second arms 116a and 116b extend from the first and second followers 114a and 114b, respectively; and (ii) a second portion 115 that extends from the terminus of the first portion 113 to free ends of the first and second followers 114a and 114b, respectively. In respect of each of the first and second follower 114a and 114b, the first portion 113 is releasably secured to the second portion 115.

Figure 10:
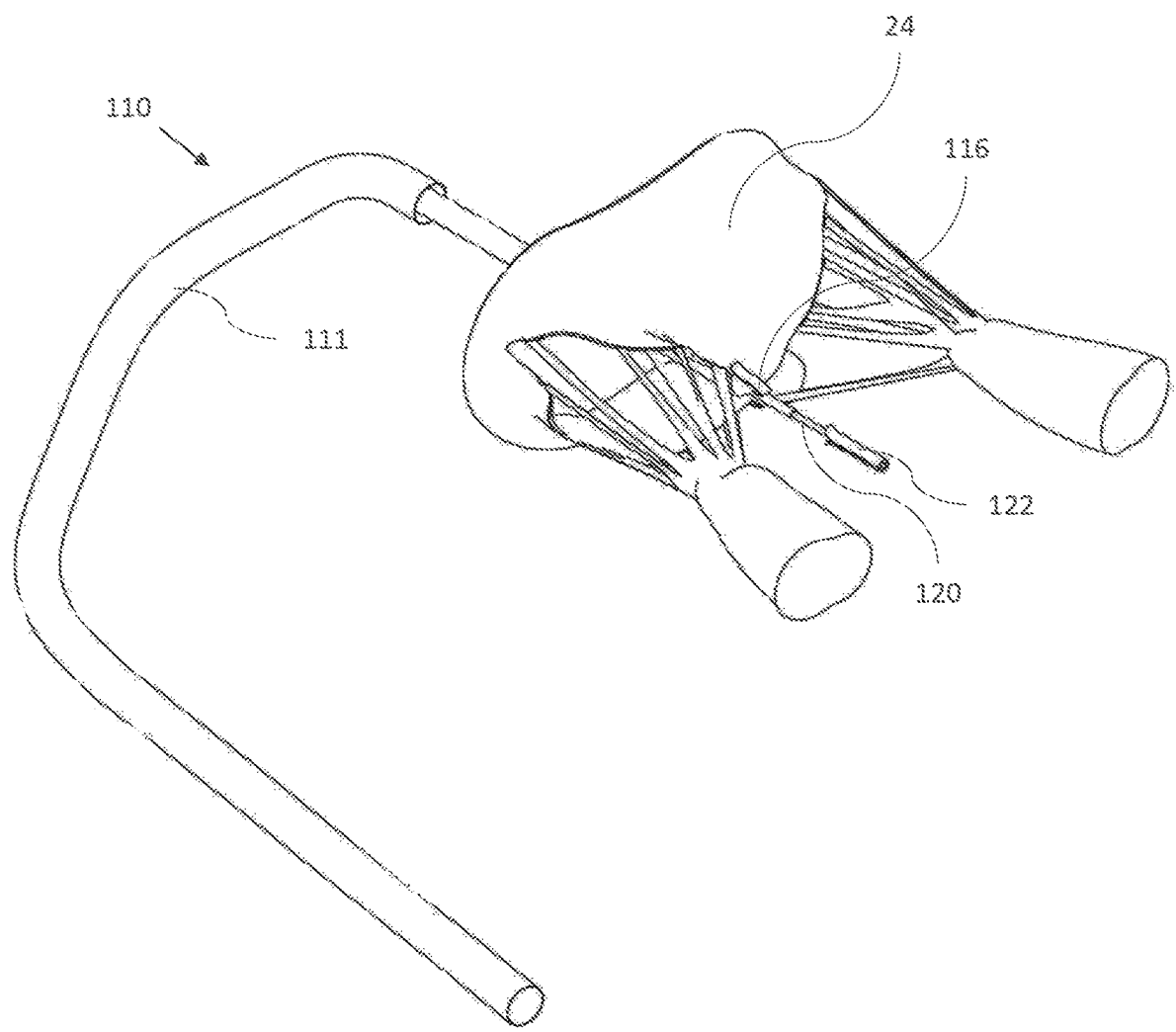
FIG. 10 is a perspective view of the valve leaflet connecting device in FIG. 9, with the followers in a closed condition.
Figure 11:
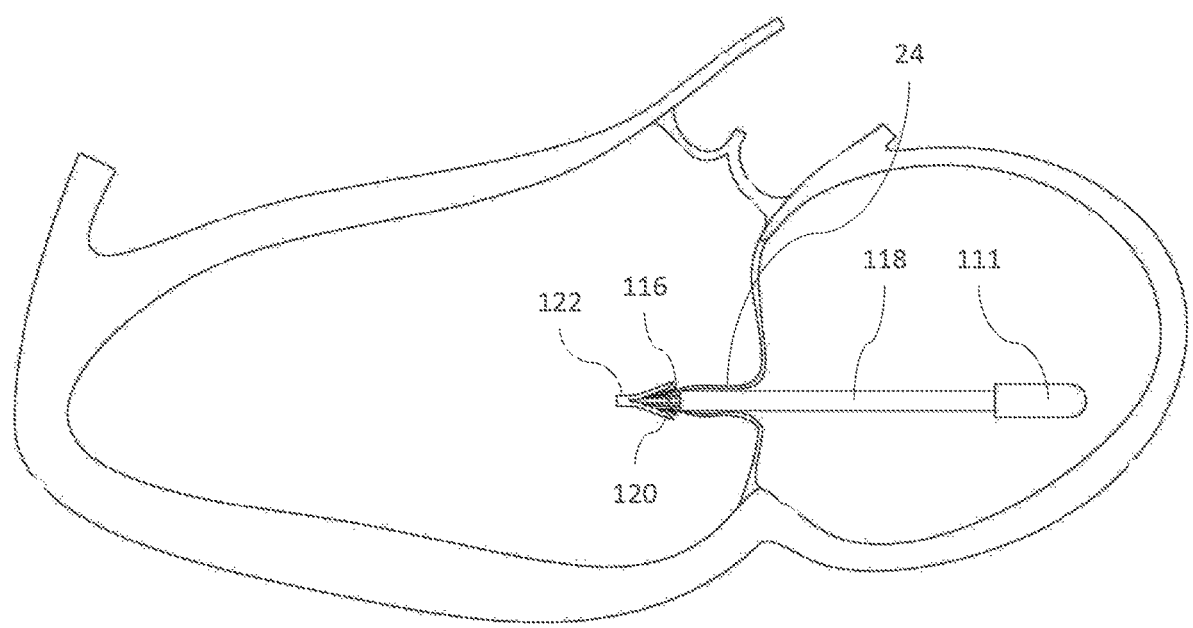
FIG. 11 is a cross-sectional side view of the valve leaflet connecting device in FIG. 9, with a positioner locating a fastener over mitral valve leaflets.
Figure 12:
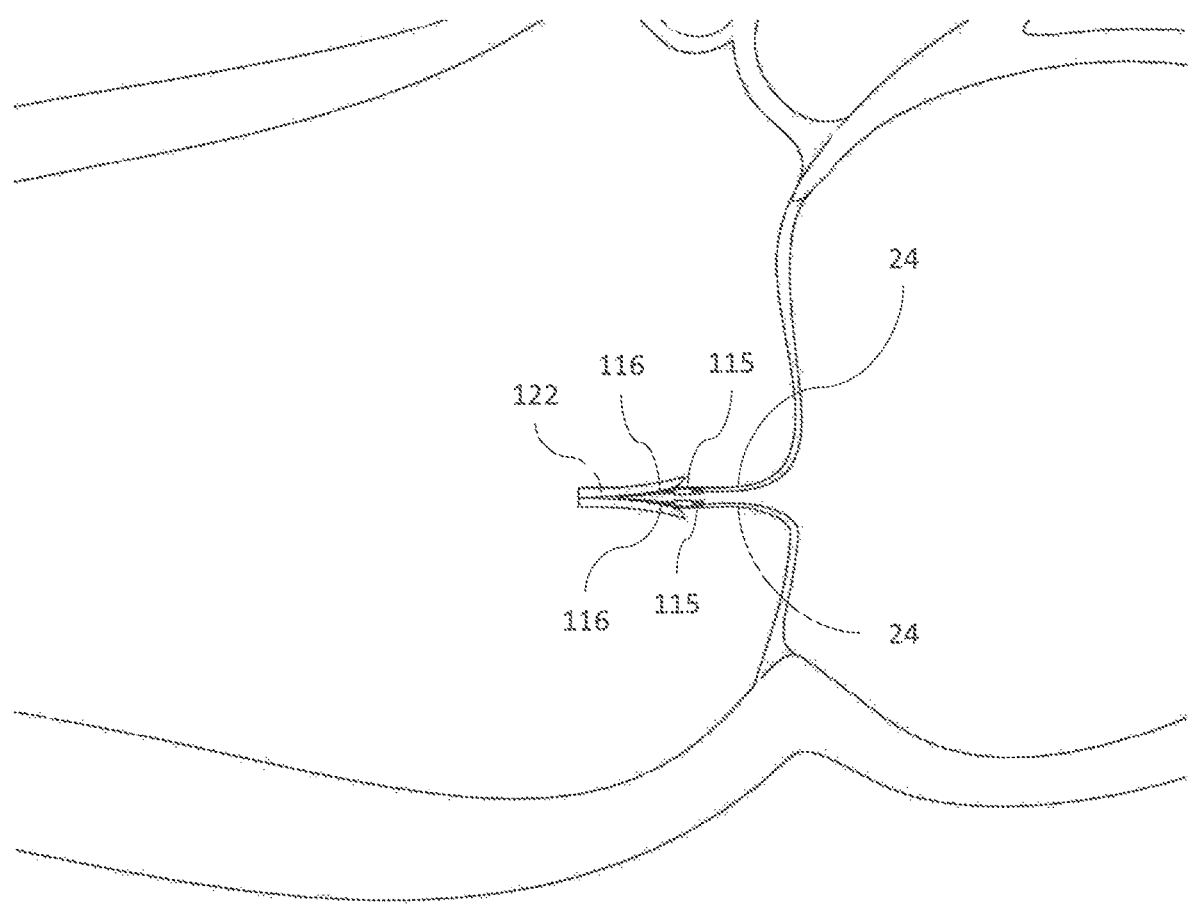
FIG. 12 is a cross-sectional side view of the valve leaflet connecting device in FIG. 9, after detachment of the fastener.

In contrast to the preferred embodiment, the followers are not bifurcated and the fastener 122 according to this second embodiment is aligned with the first and second arms 116a and 116b, such that when the follower arms 114 are moved to the closed condition (as shown in FIG. 10): (i) the first and second arms 116a and 116b may be received between the fastener 122 jaws when the fastener 122 jaws are in the splayed condition; and (ii) subsequent movement of the fastener 122 jaws towards the securing condition causes the first and second arms 116a and 116b to clamp towards the second portions 115 of the first and second followers 114a and 114b, respectively, to capture a valve leaflet 24 between an arm 116 and a second portion 115 of a corresponding follower 114. This is illustrated in FIG. 11. Turning to FIG. 12, with the valve leaflets 24 clamped by the fastener 122 via the arms 116 and the second portions 115 of the followers 114, the second portions 115 of the followers 114 are disconnected from the first portions of the followers 113 to permit the valve leaflet connecting device 110 (excluding the second portion 115 of the followers 114, the arms 116 and the fastener 122) to be removed from the patient's vasculature or anatomy.

Figure 13:
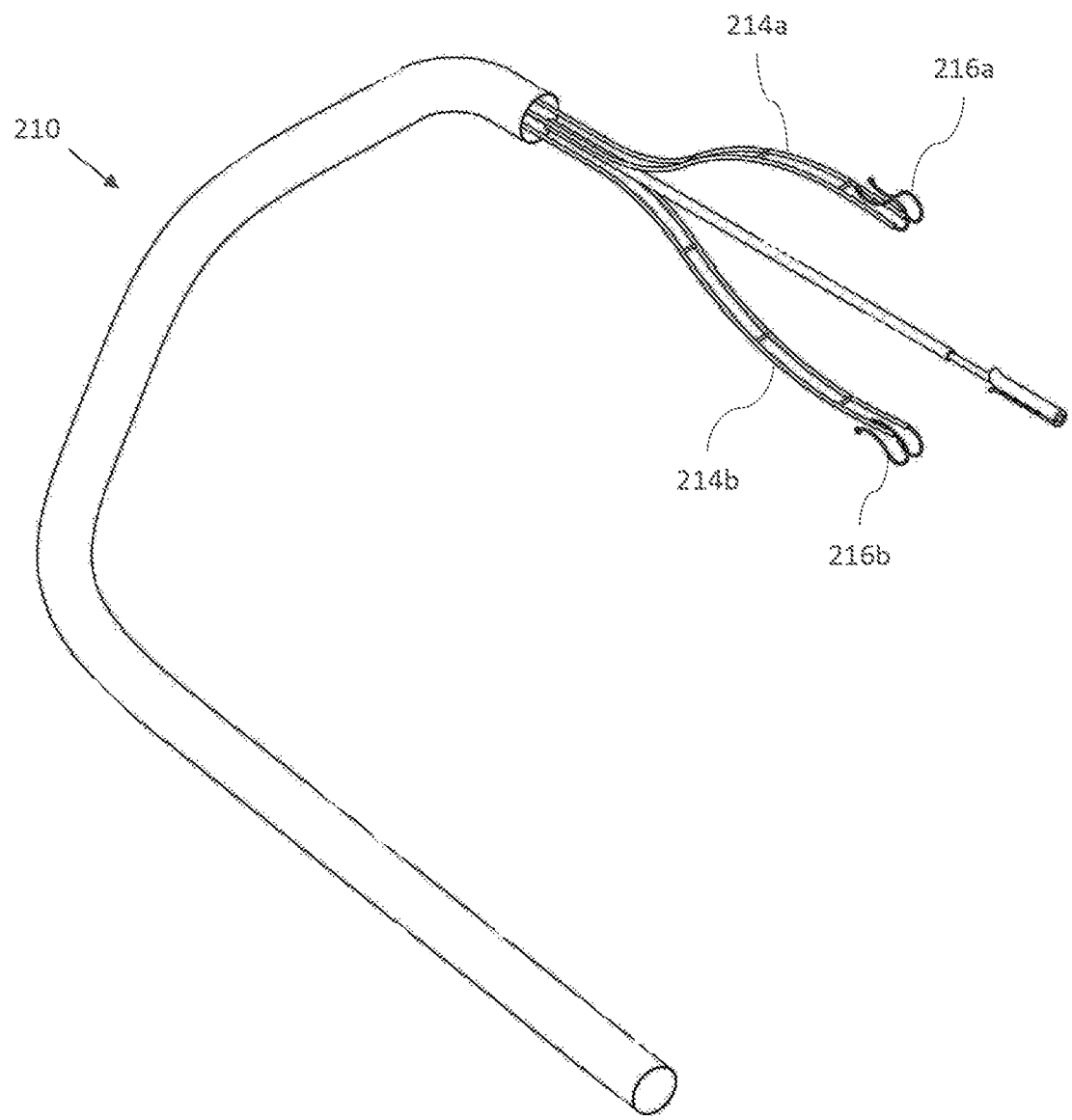
FIG. 13 is a perspective view of a valve leaflet connecting device according to a third embodiment of the invention.

According to a third embodiment of the valve leaflet connecting device 210 shown in FIG. 13, the first and second arms 216a and 216b are resilient and are axially retractable within, and extendable from the first and second followers 214a and 214b, respectively. Such an arrangement is an alternative to the second embodiment of the valve connecting device 110, which requires the second portions 115 of the followers 114 to be dis-connectable from the first portions 113 of the followers 114.

It will be appreciated that for each of the embodiments of the valve leaflet connecting device 10, 110 and 210, movement of the followers 14, 114, 214 relative to each other does not result in relative movement of the followers 14, 114 and 214 on the one hand and associated arms 16, 116 and 216 on the other hand.

The invention claimed is:

1. A valve leaflet connecting device including:
a base that defines a longitudinal axis;
first and second followers extending from the base;
a first arm on the first follower, which first arm extends from the first follower in a direction away from the second follower and away from the base to define an acute angle between the first follower and first arm for capturing a first leaflet there between;
a second arm on the second follower, which second arm extends from the second follower in a direction away from the first follower and away from the base to define an acute angle between the second follower and second arm for capturing a second leaflet there between;
the first and second followers being resiliently deformable between:
an open condition, in which:
a first virtual line that: intersects the point from which the first arm extends from the first follower; and runs parallel to the longitudinal axis of the base; and
a second virtual line that: intersects the point from which the second arm extends from the second follower; and runs parallel to the longitudinal axis of the base,
wherein the first and second virtual lines are spaced apart by more than 15 mm; and
a closed condition, in which the first and second virtual lines are spaced apart by less than 5 mm; and
deforming means for deforming the followers towards the closed condition,
such that, in use:
(i) the first and second followers may be: passed axially through a valve, between first and second valve leaflets; and resiliently deformed by a force applied to the first and second followers by the valve leaflets as the valve leaflets open and close;
(ii) the first arm may capture the first leaflet between the first arm and the first follower, and the second arm may capture the second leaflet between the second arm and the second follower, with the first and second followers disposed between the first and second leaflets; and
(iii) the deforming means may deform the first and second followers towards the closed condition, thereby moving the first and second leaflets towards each other.

2. A valve leaflet connecting device according to claim 1, further including:
a positioner extending from the base, between the first and second followers; and
a fastener releasably secured to the positioner, which fastener includes first and second fastener jaws that:
extend away from the base; and
are movable between: (i) a splayed condition in which leaflets may be received between the first and second fastener jaws; and (ii) a securing condition in which the first and second fastener jaws secure the leaflets there between, such that, in use, when first and second leaflets are moved towards each other:
(i) the fastener may receive the first and second leaflets between the fastener jaws when the fastener jaws are in the spayed condition; and
(ii) moving the fastener jaws towards the securing condition secures the first and second leaflets to each other.

3. A valve leaflet connecting device including:
a base that defines a longitudinal axis;
first and second followers extending from the base;
a first arm on the first follower, which first arm extends from the first follower in a direction away from the second follower and towards the base to define an acute angle between the first follower and first arm for capturing a first leaflet there between;
a second arm on the second follower, which second arm extends from the second follower in a direction away from the first follower and towards the base to define an acute angle between the second follower and second arm for capturing a second leaflet there between;
the first and second followers being resiliently deformable between:
an open condition, in which:
a first virtual line that: intersects the point from which the first arm extends from the first follower; and runs parallel to the longitudinal axis of the base; and
a second virtual line that: intersects the point from which the second arm extends from the second follower; and runs parallel to the longitudinal axis of the base,
wherein the first and second virtual lines are spaced apart by more than 15 mm; and
a closed condition, in which the first and second virtual lines are spaced apart by less than 5 mm; and
deforming means for deforming the followers towards the closed condition,
such that, in use:
(i) the first and second followers may be: passed axially through a valve, between first and second valve leaflets; and resiliently deformed by a force applied to the followers by the valve leaflets as the valve leaflets open and close;
(ii) the first arm may capture the first leaflet between the first arm and the first follower, and the second arm may capture the second leaflet between the second arm and the second follower, with the first and second followers disposed between the first and second leaflets; and
(iii) the deforming means may deform the first and second followers towards the closed condition, thereby moving the first and second leaflets towards each other.

4. A valve leaflet connecting device according to claim 3, further including:
a positioner extending from the base, between the first and second followers; and
a fastener releasably secured to the positioner, which fastener includes first and second fastener jaws that:
extend towards the base; and
are movable between: (i) a splayed condition in which leaflets may be received between the first and second fastener jaws; and (ii) a securing condition in which the first and second fastener jaws secure the leaflets there between,
such that, in use, when first and second leaflets are moved towards each other:
(i) the fastener may receive the first and second leaflets between the fastener jaws when the fastener jaws are in the spayed condition; and
(ii) moving the fastener jaws towards the securing condition secures the first and second leaflets to each other.

5. A valve leaflet connecting device according to claim 2, wherein:
the first arm extends from the first follower by at least 3 mm; and
the second arm extends from the second follower by at least 3 mm.

6. A valve leaflet connecting device according to claim 5, further including a catheter, and wherein the base is disposed at, or defined by a first axial end of the catheter.

7. A valve leaflet connecting device according to claim 6, wherein the first and second followers and the positioner: (i) extends from an axially extending lumen defined by the catheter and the base; and (ii) are movable axially along the axially extending lumen defined by the catheter.

8. A valve leaflet connecting device according to claim 7, further including control means at or near a second axial end of the catheter for:
controlling relative axial movement of the catheter on the one hand and the first and second followers on the other hand;
controlling relative axial movement of the catheter and the positioner, thereby to vary the position of the fastener relative to the first and second arms; and
controlling movement of the fastener jaws from the splayed condition to the securing condition.

9. A valve leaflet connecting device according to claim 8, wherein the first arm is hingedly connected to the first follower and the second arm is hingedly connected to the second follower.

10. A valve leaflet connecting device according to claim 9, wherein the first and second arms are movable along the first and second followers, respectively.

11. A valve leaflet connecting device according to claim 10, wherein the first arm is movable along the first follower independently of movement of the second arm along the second follower.

12. A valve leaflet connecting device according to claim 11, further including clamping means for moving the first and second arms from: (i) a receiving condition, in which free ends of the first and second arms are spaced from the first and second followers, respectively, for receiving leaflets there between; and (ii) a clamped condition, in which the first and second arms are biased towards the first and second followers, respectively, for clamping leaflets there between.

13. A valve leaflet connecting device according to claim 12, wherein operation of the clamping means is independent of operation of the deforming means.

14. A valve leaflet connecting device according to claim 13, wherein each of the first and second followers define: (i) a diverging zone proximal the base, along which diverging zone the first and second followers diverge from each other as they extend from the base; and (ii) a converging zone, along which the first and second followers converge towards each other as they extend from the end of the diverging zone distal the base.

15. A valve leaflet connecting device according to claim 14, wherein: (i) the diverging zones on the first and second followers extend from the base to the first and second arms, respectively; and (ii) the converging zones on the first and second followers extend from the first and second arms, respectively to free ends of the first and second followers.

16. A valve leaflet connecting device according to claim 4, wherein:
   each of the first and second followers comprises: (i) a first portion that extends from the base and terminates prior to the points at which the first and second arms extend from the first and second followers, respectively; and (ii) a second portion that extends from the terminus of the first portion to free ends of the first and second followers, respectively; and
   in respect of each of the first and second follower, the first portion is releasably secured to the second portion.

17. A valve leaflet connecting device according to claim 16, wherein the fastener is aligned with the first and second arms, such that: (i) the first and second arms may be received between the fastener jaws when the fastener jaws are in the splayed condition; and (ii) subsequent movement of the fastener jaws towards the securing condition causes the first and second arms to clamp against the first and second followers, respectively.

18. A valve leaflet connecting device according to claim 4, wherein the first and second arms are resilient and are axially retractable within, and extendable from the first and second followers, respectively.

19. A valve leaflet connecting device according to claim 2, wherein each of the first and second followers is bifurcated towards its free end, for receiving the fastener between the bifurcations.

20. A valve leaflet connecting device according to claim 5, further including hingedly connected stabilising jaws disposed between the first and second followers, the ends of the stabilising jaws distal the hinge being connected to the first and second followers and the hinged connection of the stabilising jaws being:
   located between the first and second followers; and
   spaced from the base,
such that deformation of the first and second followers between the open and closed conditions causes the hinged connection of the stabilising jaws to displace relative to the base.

21. A valve leaflet connecting device according to claim 20, further including resisting means for resisting displacement of the hinged connection of the stabilising jaws relative to the base, thereby to vary stiffness of the first and second followers.

* * * * *